United States Patent [19]

Masuda

[11] Patent Number: 5,120,512
[45] Date of Patent: Jun. 9, 1992

[54] APPARATUS FOR STERILIZING OBJECTS TO BE STERILIZED

[76] Inventor: Senichi Masuda, No. 415, Nishigahara 3-2-1, Kita-ku, Tokyo, Japan

[21] Appl. No.: 584,480

[22] Filed: Sep. 18, 1990

Related U.S. Application Data

[63] Continuation of Ser. No. 159,691, Feb. 24, 1986, abandoned.

[51] Int. Cl.$^5$ .................. A61L 2/20; C01B 13/10
[52] U.S. Cl. ..................... 422/297; 55/279; 123/45 R; 422/30; 422/31; 422/198; 422/295; 422/298; 422/305
[58] Field of Search ........... 422/31, 37, 28-31, 422/300, 198, 116, 292, 295, 297, 305, 307, 186.07, 4-5; 123/45 R; 55/279

[56] References Cited

U.S. PATENT DOCUMENTS

| | | | |
|---|---|---|---|
| 1,126,430 | 1/1915 | Elliot | 422/31 X |
| 1,932,379 | 10/1933 | Ballentine | 422/30 X |
| 2,226,145 | 12/1940 | Smith | 422/29 X |
| 3,117,832 | 1/1964 | Thomas | 422/29 X |
| 3,372,980 | 3/1968 | Satas | 422/31 X |
| 3,443,884 | 5/1969 | Linder | 422/298 |
| 3,678,955 | 7/1972 | Nelson | 422/31 X |
| 3,719,017 | 3/1973 | Shapiro et al. | 422/28 X |
| 3,897,210 | 7/1975 | Gruber et al. | 422/31 |
| 4,309,388 | 1/1982 | Tenney et al. | 422/30 X |
| 4,337,223 | 6/1982 | Kaye | 422/30 X |
| 4,400,357 | 8/1983 | Hohmann | 422/297 |
| 4,517,159 | 5/1985 | Karlson | 422/30 X |
| 4,687,635 | 8/1987 | Kaehler et al. | 422/110 X |
| 4,752,444 | 6/1988 | Bowen et al. | 422/28 |
| 4,889,539 | 2/1989 | Firey et al. | 422/111 X |
| 4,909,999 | 3/1990 | Cummings et al. | 422/30 |
| 4,919,104 | 4/1990 | Hensel et al. | 123/45 R X |

FOREIGN PATENT DOCUMENTS

| | | | |
|---|---|---|---|
| 0561205 | 9/1932 | Fed. Rep. of Germany | 422/87 |
| 3416743 | 7/1985 | Fed. Rep. of Germany | 422/292 |
| 8000413 | 3/1980 | World Int. Prop. O. | 422/292 |

Primary Examiner—Robert J. Warden
Assistant Examiner—Amalia Santiago
Attorney, Agent, or Firm—Price, Heneveld, Cooper, DeWitt & Litton

[57] ABSTRACT

A method for sterilizing objects to be sterilized is disclosed, in which an object to be sterilized such as a hand piece is preliminarily brought into a wetted state, and then accommodated and air-tightly closed up within a sterilizing chamber communicated with an oxygen cylinder, oxygen fed from the oxygen cylinder is introduced into an ozonizer to produce ozonized oxygen gas having an ozone concentration of at least 10000 ppm, preferably 15000 ppm or higher, then the ozonized oxygen as is made to pass through the sterilizing chamber after it has been heated up to perfectly replace air within the sterilizing chamber by the ozonized oxygen gas, also moisture adhered to the objects to be sterilized is partly evaporated, subsequently the communication between the sterilizing chamber and the oxygen source is interrupted, the ozonized oxygen gas is circulated through the sterilizing chamber and the ozonizer while it is heated up at the inlet of the sterilizing chamber to thereby enhance the ozone concentration up to at least 20000 ppm, preferably up to 30000 ppm or higher without consuming oxygen, and meanwhile, bacteria adhered to the objects to be sterilized are sterilized surely in a short period of time by the ozone gas under an inflated and wetted condition of the bacteria.

7 Claims, 4 Drawing Sheets

APPARATUS FOR STERILIZING OBJECTS TO BE STERILIZED

This application is a continuation of application Ser. No. 07/159,691 filed Feb. 24, 1988, now abandoned.

BACKGROUND OF THE INVENTION:

1. Field of the Invention:

The present invention relates to a method and an apparatus for sterilizing bacteria adhered to a surface of a hand piece to be used by a dentist for treating a patient and to an inner surface of an air communication bore therein and bacteria adhered to other objects to be sterilized by means of ozone gas.

2. Description of the Prior Art:

Heretofore, in a sterilizing apparatus for such type of objects, generally sterilization has been carried out through high-temperature heating with steam under high pressure by use of an autoclave. However, since the hand piece for a dentist is composed of precise mechanical parts such as a chuck for mounting and dismounting a small drill, an air turbine for rotating this chuck at a high speed, a device for cooling the tip end of the drill and the like, there is a fear that the precision may be possibly lost by distortion occurring upon high-temperature heating. Consequently, disinfection and sterilization cannot be carried out sufficiently, and it is surmised that a hygienically serious problem may be caused.

Furthermore, a time of about 15 minutes for heating an object to a temperature that is necessary for sterilization (about 130° C.), a time of about 20 minutes for sterilizing perfectly at that temperature and a time of about 10 minutes for cooling the object, that is, a total time of at least about 45 minutes was necessitated. Hence quick sterilization of a hand piece could not be achieved, and this was quite inconvenient.

Besides the above-mentioned sterilizing apparatus, among the sterilizing apparatuses for the above-described type of objects an apparatus employing ethylene oxide gas is also known, but in this case also, a sterilizing time of at least 50 minutes and, in addition, repeated pressurizing and depressurizing operations for that gas were necessitated. Moreover, there was the shortcoming that ethylene oxide gas which is poisonous and carcinogenic might remain on a hand piece.

Though it can be conceived to carry out sterilization by use of high-concentration ozone gas having a strong sterilizing power and no residual poisonousness in order to avoid the above-mentioned problems, in many cases a hand piece just after treatment of a patient would have its surface wetted and coated with a water film, and so, even if the hand piece under such condition is placed in ozone gas within a sterilizing chamber, the ozone gas would not fully reach bacteria in the water film and perfect sterilization was difficult.

In addition, in the case of certain ones of the bacteria which can be hard to sterilize if the bacteria adhered to the surface of the hand piece are placed under a condition at a temperature lower than a room temperature or held in a dried condition, especially in the case of hey bacillus (*Bacillus subtilis*), since in their spore a cell membrane forming an outer wall of protoplasm maintains a dense shell structure, ozone gas is intercepted by the shell and cannot penetrate through the shell and reach the protoplasm therein. Therefore, it becomes very difficult to sterilize the bacteria. Furthermore, although it is relatively easy to sterilize a surface of a hand piece because it can be easily exposed to ozone gas, since an inner surface of an air communicating bore in a hand piece can be only partially exposed to ozone gas, it is practically very difficult to sterilize the inner surface.

SUMMARY OF THE INVENTION

It is, therefore, an object of the present invention to resolve the above-mentioned respective problems of carrying out sterilization by high-temperature heating with an autoclave or by making use of ethylene oxide gas or ozone gas, and especially to most effectively sterilize even spores of bacteria adhered to a hand piece.

Another object of the present invention is to preclude the above-described difficulties encountered in the case of sterilizing a hand piece under a wetted condition just after treatment by means of ozone gas and the adverse effect upon human bodies in the case of employing high-concentration ozone gas.

Still another object of the present invention is to provide an apparatus which facilitates sterilization of the surface of a hand piece as the well as an inner surface of an air communicating bore therein.

A further object of the present invention is to improve the gas producing efficiency of an ozonizer and to design it in a compact form.

According to one feature of the present invention, there is provided a method for sterilizing objects to be sterilized such as a hand piece for use by a dentist, which consists of the steps of placing the objects to be sterilized such as a hand piece or the like within an airtight sterilizing chamber communicated with an oxygen source such as an oxygen cylinder after they have been preliminarily caused to have a wetted condition and producing an ozonized oxygen gas having an ozone concentration of 10000 ppm or higher, preferably of 15000 ppm or higher by introducing oxygen fed from that oxygen source to an ozone generator, then completely replacing the air within the sterilizing chamber with a mixture of ozone and oxygen and also partly evaporating moisture adhered to the above-mentioned objects to be sterilized such as a hand piece or the like by making the thereby produced ozone and oxygen gas mixture pass through the sterilizing chamber after it has been heated. Subsequently interrupting the communication between the sterilizing chamber and the ozone and oxygen source and circulating the produced ozone and oxgen gas mixture through the sterilizing chamber and the ozonizer while the ozone/oxygen gas is mixture being heated at an inlet of the sterilizing chamber to thereby enhance the ozone concentration at least up to 20000 ppm, preferably up to 30000 ppm or higher without consuming oxygen, and sterilizing bacteria adhered to the objects to be sterilized such as a hand piece or the like under an inflated and wetted condition by the above-mentioned ozone gas during the circulation period.

According to another feature of the present invention, there is provided an apparatus for sterilizing objects to be sterilized such as a hand piece for use by a dentist, wherein an oxygen source communicates with one side of a sterilizing chamber via a heater and an ozonizer. An exhaust valve leading to the atmosphere communicates with the other side of the sterilizing chamber via an ozone degenerator for decomposing residual ozone. Further the ozonizer is coupled to the sterilizing chamber so that circulation of ozone/oxygen gas through the heater, the ozonizer and a circulating pump can be accomplished. The sterilizing chamber, the ozone decomposer, an ozone monitor and a circulating pump are communicated with one another so that circulation of the ozone and oxygen gas can be effected therethrough.

According to still another feature of the present invention, in the above-featured sterilizing apparatus, a receiving seat into which a base portion of a hand piece can be air-tightly inserted is provided within the sterilizing chamber. A communicating bore adapted to communicate with a communicating bore in the hand piece is formed in the receiving seat. The communicating bore is connected to a switching exhaust valve, one outlet of which switching exhaust valve communicates with the outer atmosphere through the ozone decomposer and, the other outlet of the same switching exhaust valve communicates with an inlet side of the ozonizer through a circulating pump. Thereby it is possible to exhaust the ozone and oxygen gas introduced into the sterilizing chamber through the interior of the communicating bore in the hand piece to the outer atmosphere or to feed it to the inlet of the ozonizer to cause to circulate therethrough.

In operation, a hand piece for dental use is placed within a sterilizing chamber after its surface has been preliminarily caused to be in a wetted condition by wiping it with wet sanitary cotton or wet paper napkin. A door of the chamber is closed, oxygen fed from an oxygen source is passed through an ozone and to produce ozonized oxygen gas having an ozone concentration of at least 10000 ppm, preferably 15000 ppm, after the gas so produced has been heated to a temperature range of 30°-70° C., preferably a temperature in the proximity of 50° C. This gas is fed into the sterilizing chamber. Then this gas is discharged to the outside via an ozone decomposer, and thereby air within the sterilizing chamber is completely replaced by the ozone and oxygen gas mixture. During this period, the remaining water film adhering to the surface of the hand piece and onto the inner surface of the air communication bore therein evaporates. Ozone is then adsorbed by the surface, resulting in formation of an ozone-water surface layer and a rise of the temperature of the water film, and inflation and wetting of the shell of the cell membrane of bacteria existing in the water film commences. Subsequently, while the above-mentioned ozone and oxygen gas is being heated at the inlet of the sterilizing chamber, it is circulated through the ozonizer and the sterilizing chamber to enhance the ozone concentration of the ozone and oxygen gas within the sterilizing chamber up to at least 20000 ppm, preferably up to 30000 ppm or higher. Then an ozone-water surface layer having a still high concentration is formed by means of the high-concentration ozone gas. Thus, as the drying process of the water film proceeds, this ozone-water surface layer comes into contact with all the bacteria which would become exposed on the surface of the hand piece and on the inner surface of the air communication bore therein and enters the interior of the cell of the bacterium after penetrating through the outer shell in the inflated and wetted condition. It effectively sterilizes all the bacteria. After this sterilizing process has been finished, the ozonizer is stopped, the sterilizing chamber is caused to communicate with the ozone decomposes and, then the ozone and oxygen gas having finished sterilization in the sterilizing chamber is passed through the ozone decomposer, an ozone sensor and the sterilizing chamber by any appropriate method such as operating a circulating pump or the like. During this period, in the ozone decomposer the ozone gas is removed by decomposition of the ozone gas by heating or by a catalyst, or by adsorption of the ozone gas by an adsorbent. The amount of residual ozone is detected by the ozone sensor, in the sterilizing chamber, the ozone gas having a high concentration is replaced by the ozone gas having a low concentration at the downstream of the ozone decomposer through a scavenging action, and the concentration is gradually lowered. After it has been confirmed by the ozone monitor that the concentration has been so lowered that the ozone is harmless for human bodies, the door of the sterilizing chamber is opened, and the sterilized hand piece is taken out to be used again for treatment of a patient.

Figure 1:
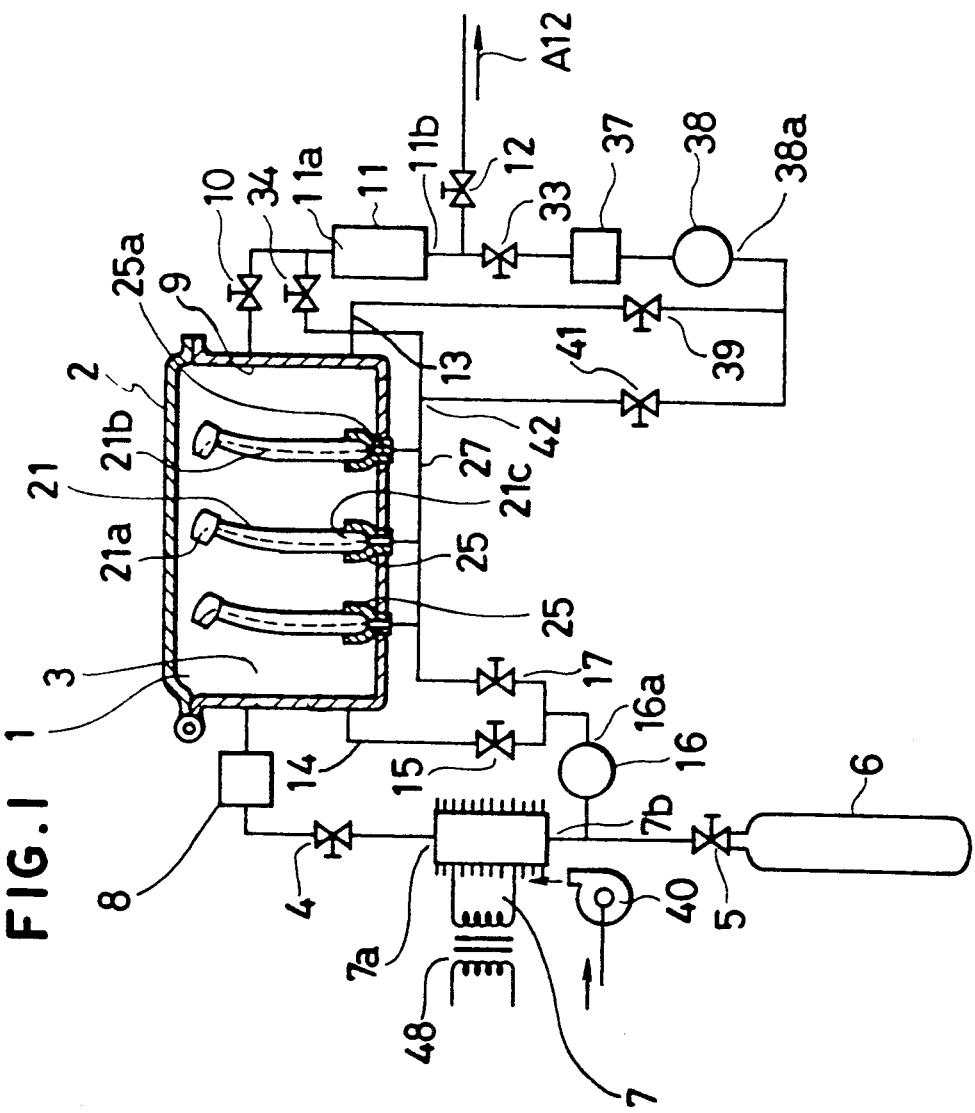
FIG. 1 is a gas flow circuit diagram of a sterilizing apparatus for practicing the method of sterilization according to the present invention.
Figure 2:
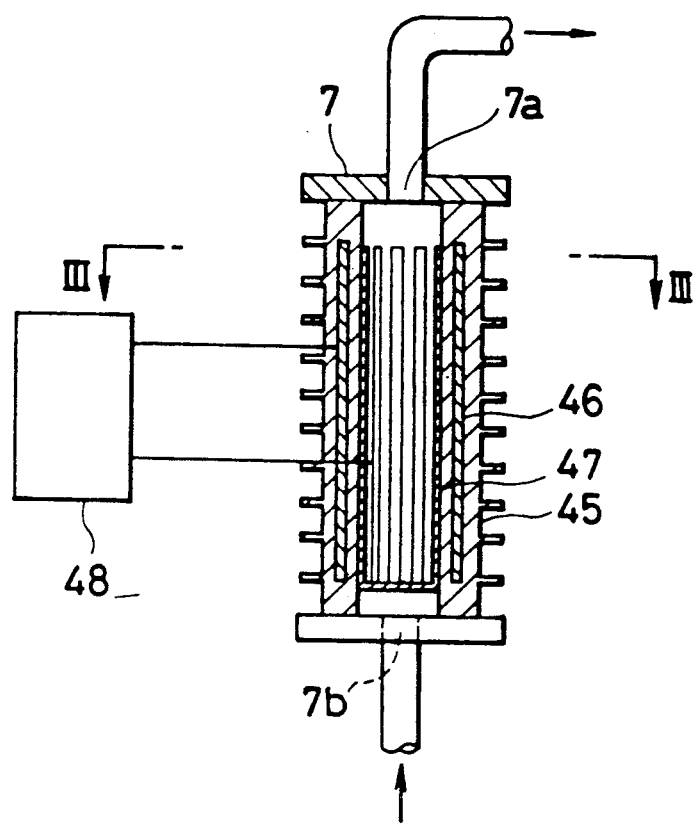
FIG. 2 is an enlarged longitudinal cross-sectional view of a part of the apparatus shown in FIG. 1.
Figure 3:
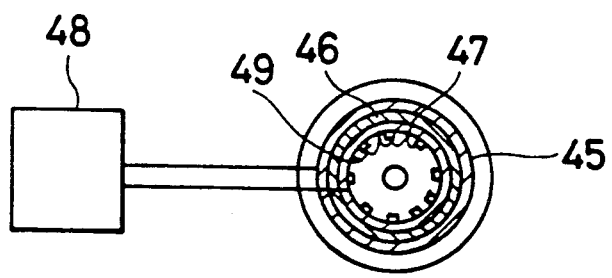
FIG. 3 is a transverse cross-section view taken along line III—III in FIG. 2.

DESCRIPTION OF THE PREFERRED EMBODIMENTS:

FIGS. 1 to 3 illustrate a sterilizing apparatus for practicing the method for sterilization according to the present invention. With reference to these figures, in a sterilizing chamber 1, the base portions 21c of hand pieces 21 held in a condition wetted by a water film adhering thereto after saliva, blood and the like of a patient have been wiped out with wetted sanitary cotton, wetted paper napkin, wetted paper towel or the like, mounted in the chamber by being air-tightly fitted into receiving seats 25, and a lid 2 is sealingly closed. The receiving seat 25 has a communicating bore 25a which communicates with a suction pipe 27. This suction pipe 27 is connected to an inlet 7b of an ozone and 7 via a valve 17 and a circulating pump 16 and connected to an inlet 11a of an ozone decomposer 11 via a valve 34. In addition, the suction pipe 27 is further connected to an outlet 11b of the ozone decomposer 11 via a valve 41, a circulating pump 38, an ozone monitor 37 and a valve 33.

Furthermore, the above-mentioned sterilizing chamber is provided with another gas inlet 13, which is connected to an outlet 38a of the circulating pump 38 via a valve 39. The sterilizing chamber is further provided with still another gas outlet 14, which is connected to an inlet 16a of the circulating pump 16 via a valve 15.

Reference numeral 40 designates a fan for cooling the ozone and 7.

At first, valves 4 and 5 are opened to make oxygen gas fed from an oxygen source 6 such as an oxygen cylinder pass through the ozone and 7 to produce ozonized oxygen gas having an ozone concentration of at least 10000 ppm. Thereafter the ozone and oxygen gas so produced is heated in a heater 8, the heated gas is fed into the sterilizing chamber 1 through a gas inlet 3 provided on one side of the sterilizing chamber 1 and passes through the sterilizing chamber 1. The gas passes through a gas exhaust port 9 provided on the other side of the sterilizing chamber 1, and, after it has passed through an exhaust valve 10 coupled to the gas exhaust port 9, the ozone decomposer 11 and a valve 12, oxygen gas having had the ozone removed therefrom is exhausted into the atmosphere in the direction of arrow A12. At this moment, valves 15, 17, 33, 34, 39 and 41 are held closed.

Thereby, air existed within the sterilizing chamber is replaced by a mixture of ozone and oxygen gas.

Figure 4:
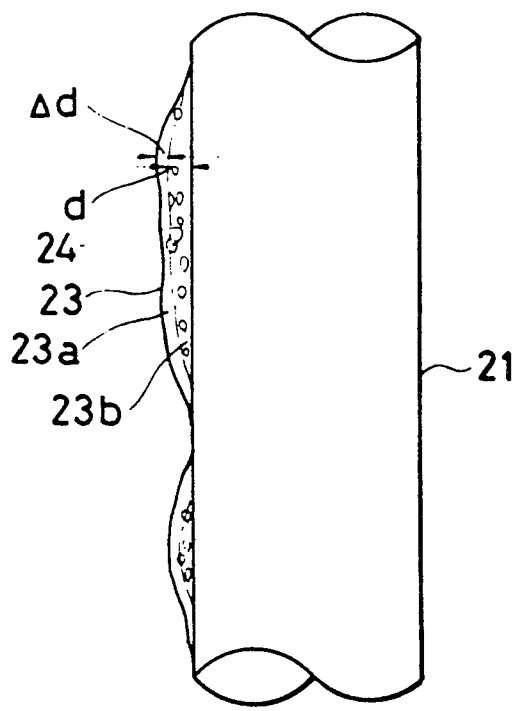
FIG. 4 is an enlarged cross-section view of a part of a hand piece in the apparatus shown in FIG. 1.

During this period, a water film 23 adhering to the surface of the hand piece 21 is evaporated by the heated ozone and oxygen gas passing through the sterilizing chamber 1, and the thickness of the water film layer is reduced by Δd from the thickness of Δd+d and thinned up to d as shown in FIG. 4.

Through this process, a surface layer 30 of the water film 23 absorbs ozone and a thin ozone-water layer 31 having a strong sterilizing power is formed here, but in its inner water layer 32, invasion of ozone does not occur, and since ozone-water is not produced therein, a sterilizing effect by ozone is not present there. Accordingly, at this step of the process, bacteria 24 in a greater part of the inner water layer 32) except for the part of the surface layer 30, would not be subjected to a sterilizing effect.

However, the temperature of the water film 23 rises as a result of contact with the heated ozone and oxygen gas. Consequently the cell membrane of the bacterium is heated under a wetted condition. resulting in inflation and wetting of the shell of the bacterium, and so, ozone it becomes easy for the ozone-water to invade the interior by penetrating through the shell.

Next, when the valve 34 is opened and the valve 10 is closed, the heated, ozone and oxygen gas introduced into the sterilizing chamber 1 enters through a head 21a of the hand piece 21 into an air communication bore 21 therein. It then passes through the above-described communicating bore 25a, suction pipe 27, valve 34 and ozone decomposer 11 and is discharged to the outer atmosphere with the ozone content removed. During this period, with respect to the water film adhered to the inner surface of the communicating bore and bacteria in the water film, partial evaporation of a water film, formation of a water surface layer, and inflation and wetting of a shell of the bacteria cell membrane are effected similarly to the above-described operation.

Subsequently, while repeating the operation of opening the valve 10 and closing the valve 34 and the operation of opening the valve 34 and closing the valve 10, replacement of air within the sterilizing chamber by ozone and oxygen gas is completed.

Next, by closing the valves 5, 17, 10 and 34 and opening the valve 15, the ozone and oxygen gas within the sterilizing chamber 1 is fed through the valve 15, the circulating pump 16, the ozone and 7, the valve 4 and the heater 8 into the same chamber 1 from its gas inlet port 3, and thereby it is circulated.

Then, with the valve 17 opened and the valve 15 closed, the above-described ozone and oxygen gas is made to pass through the inner communicating bore 21b of the hand piece 2 and thereafter it is fed through the valve 17, the circulating pump 16, the ozone and 7, the valve 4 and the heater 8 into the sterilizing chamber 1 via its gas inlet 3 and is thus circulated. Subsequently the operation of alternately opening and closing the valve 15 and valve 17, respectively, is repeated. In this way, the ozone and oxygen gas for sterilization use is circulated through the sterilizing chamber 1, the communicating bore 21b and the ozone and 7. During this period the ozone concentration of the ozone and oxygen gas within the sterilizing chamber 1 is increased up to at least 20000 ppm, preferably up to 30000 ppm or higher. This high-concentration ozone gas is brought into contact with the surface of water films adhered to the outer surface of the above-described hand piece 21 and the inner surface of the communicating bore. By greatly enhancing the ozone concentration of the ozone-water layer forming the surface layer the sterilizing power of the ozone-water layer can be raised greatly. Then, as the water film evaporates, bacteria 24 in the water film would be exposed gradually, and at this time the above-mentioned ozone-water layer would come into direct contact with the bacteria 24 being exposed. At this moment, under a wetted condition, the bacteria have been further inflated and wetted due to the temperature maintained by the ozone gas, and under such a condition, the high-concentration ozone would penetrate through the cell membrane extremely efficiently and would enter the interior of the bacterium, and thereby it can completely sterilize the bacteria.

Figure 5:
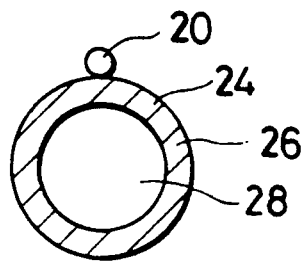
FIGS. 5, 6 and 7, respectively, are enlarged cross-section views of a bacterium.
Figure 6:
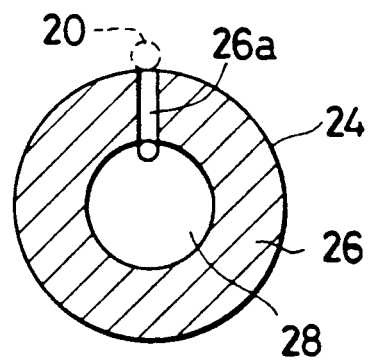
Figure 7:
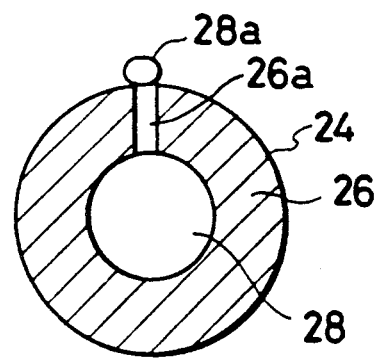

The sterilizing conditions within the sterilizing chamber at this moment are shown in FIGS. 5, 6 and 7, among which FIG. 5 is an enlarged cross-section view of a bacterium 24 in a dried state, and by way of example, a spore of a hay bacillus (*Bacillus subtilis*) is illustrated. A cell membrane forming an outside portion of protoplasm 27 of the cell is constructed of a shell 26 which forms an extremely dense biological structure. Hence even if an ozone molecule 20 should come into contact with its surface, it cannot reach the protoplasm 27 since it is intercepted by the shell 26, and so, it cannot sterilize.

In addition, FIG. 6 shows a state of the shell 26 that is wetted and inflated by applying heated ozone gas under a wetted condition. At this moment, an ozone molecule 20 on the outside of the shell 26 can quickly invade into the shell 26, the reaction speed for oxidizing the shell 26 is also very large. Hence a penetration bore 26a is formed in a short period of time and the molecule 20 passes through the bore 26a and reaches the protoplasm 27, where it can immediately and perfectly sterilize.

FIG. 7 shows the state of a sterilized bacterium 24, in which it can be confirmed with the aid of an electron microscope that a part 27a of the protoplasm 27 has been pushed out of the surface of the shell 26 through the above-described penetration bore 26a.

After the sterilization of the outer surface of the hand piece 21 as well as the inner surface of the communicating bore thereof has been finished in the above-described manner, the operation of the ozonizer 7, the circulating pump 16 and the heater 8 are stopped, the valves 4, 12, 15, 17 and 34 are closed, the valves 10, 33, 39 and 41 are opened, and the circulating pump 38 is operated. Then, the high-concentration ozone and oxygen gas in the sterilizing chamber 1 and within the communicating bore 21b of the hand piece 21 is circulated through the exhaust port 9, the valve 10, the ozone decomposer 11, the valve 33, the ozone monitor 37, the circulating pump 38, the valve 39 and the gas inlet 13, and also through the valve 41, the suction pipe 27 and the communicating bore 21b, and returns to the sterilizing chamber 1. During this period the ozone concentration of the circulated gas is quickly lowered by the action of the ozone decomposer 11.

When this ozone concentration has been reduced to such extent that it becomes harmless for human bodies, this is confirmed by the ozone monitor 37. The lid 2 of the sterilizing chamber 1 is the opened, and the hand pieces 21 accommodated therein are taken out for use.

In the above-described ozone and 7, as shown in FIGS. 2 and 3, a planar dielectric electrode 46 is buried within a cylindrical dielectric body 45, wire-shaped corona discharge electrodes 47 are disposed on the inner surface of the cylindrical dielectric body 45, and a high-frequency, high-voltage power supply 48 is connected between these respective electrodes 46 and 47. In operation, a high-frequency, high voltage is applied between these electrodes 46 and 47. Thereby creeping discharge 49 is generated on the surface of the cylindrical dielectric body 45 on the side of the wire-shaped corona discharge electrode 47 and the oxygen gas fed through its inlet 7b is transformed into ozone gas.

At this time, by cooling the ozone and 7 by means of a cooling fan 40 as shown in FIG. 1, the ozone generating efficiency of the ozone and 7 can be improved.

Figure 8:
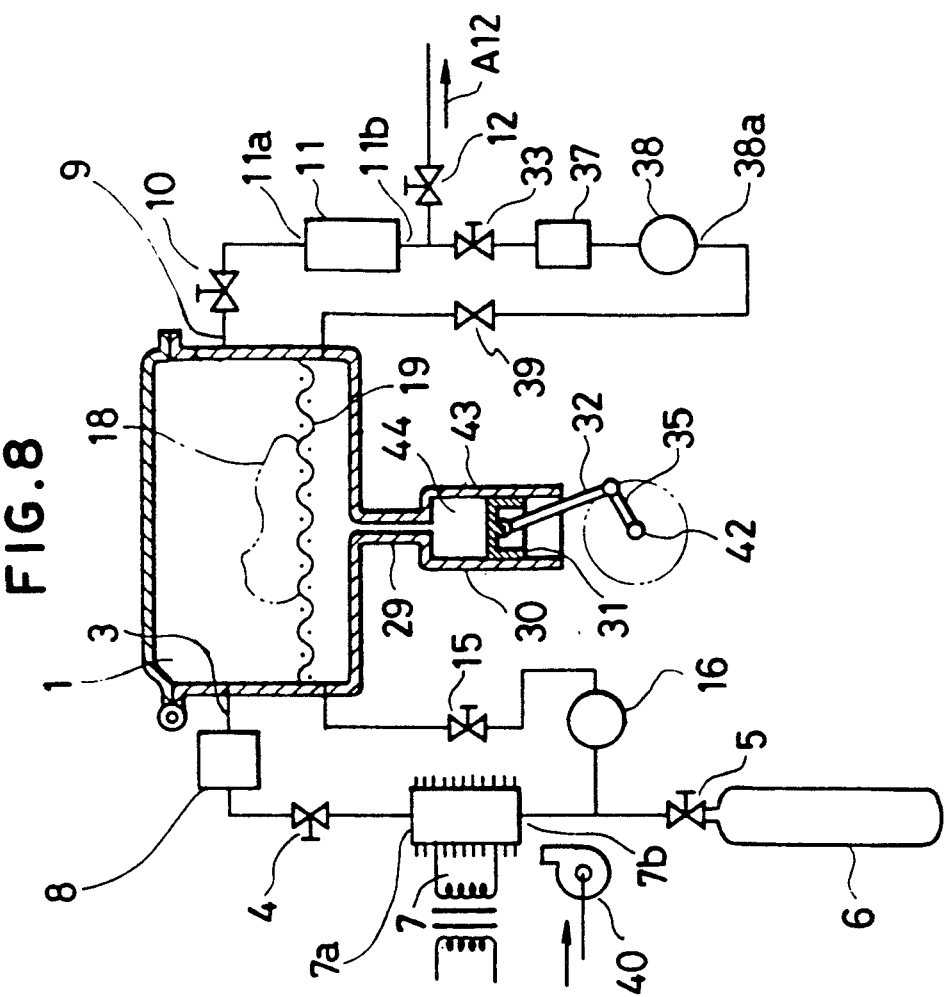
FIG. 8 is a gas flow circuit diagram of another preferred embodiment of the sterilizing apparatus according to the present invention.

A sterilizing apparatus shown in FIG. 8 forms another preferred embodiment of the present invention, in which the sterilizing chamber 1 and the pressure chamber 44 of a pressure-vibrating device 43 communicate with each other through a communicating pipe 29. In the present-vibrating device 43, a piston 31 is slidably fitted into a cylinder 30. The piston 31 and a crank shaft 42 are coupled via a connecting rod 32 and a crank arm 35. This crank shaft 42 is rotated by an electric motor or the like, and thereby the pressure variation in the pressure chamber 44 caused by reciprocation of the piston 31 within the cylinder 30 is transmitted to the sterilizing chamber 1 through the communicating pipe 29, as a vibrating force.

Thereupon, if all the valves 4, 10,39 and 15, communicating with the sterilizing chamber 1, are respectively closed with ozone and oxygen gas filling the sterilizing chamber 1, then the pressure of the ozone and oxygen gas within the sterilizing chamber 1 would be vibrated by the above-mentioned vibrating force. Consequently, an object 18 to be sterilized on a wire net 19 that has been preliminarily closed tightly in the sterilizing chamber 1 would be repeatedly subjected to pressurization and depressurization. Hence the ozone and oxygen gas would be caused to deeply enter into and exhaust from the interior and even the interstices of the object to be sterilized, and it can perfectly sterilize the bacteria existing there.

In more particular, the above-described pressure vibrating device 43 should not be limited to the above-described construction consisting of a cylinder 30 and a piston 31. In place of such a construction, a combination of a conventional diaphragm and contracting/expanding means therefor, for instance, the assembly of the crank shaft 42, crank arm 35, a connecting rod 32 and electric motor, with the cylinder 30 replaced by guide rails for the piston 31, could be employed. At this instance, an opening portion of that diaphragm is mounted to the communicating pipe 29 and the other end thereof is mounted to a slide portion corresponding to the piston 31.

It is to be noted that among the reference numerals used in the embodiment shown in FIG. 8, the same numerals as those used in FIG. 1 designate component parts having the same names and the same functions, and so, further explanation thereof has been omitted. This it will be obvious from the above description with reference to FIG. 1.

The present invention is as described above, and since an oxygen source and an ozone and are coupled by piping with a sterilizing chamber via a heater, dried heated, ozone and oxygen gas can be fed into the sterilizing chamber. Hence if a hand piece held in a wetted state is placed the sterilizing chamber, during the replacement process of the initial air in the sterilizing chamber by the ozone and oxygen gas, an ozone-water layer having a strong sterilizing power is initially formed in the surface portion of a water layer adhered to the surface of the hand piece as well as to the inner surface of the communicating bore thereof. Thereby a sterilizable condition is created, also a cell membrane or an outer shell on the surface of a bacterium can be brought into a wetted and inflated state where the bacterium can be easily sterilized.

During this process, since the ozone and oxygen gas produced in the ozone and is circulated through the interior of the sterilizing chamber, the interior of the communicating bore in the hand piece and the ozonizer while being heated especially in the next step of the process, the adhered water film is evaporated while further enhancing the ozone concentration of the above-mentioned ozone-water surface layer. Also, the inflation and wetting of the outer shell of the bacterium is further promoted, and in the process of exposing the bacteria in accordance with evaporation of the water film, the ozone-water layer having the above-mentioned strong sterilizing power is made to act upon all the bacteria and can sterilize them perfectly. In other words, the high-concentration ozone molecules in the ozone-water surface layer can easily invade the outer shell of the bacterium that has been inflated and wetted under a wetted condition, thus forming a penetration bore in the outer shell by an oxidation reaction. Hence the ozone can easily enter the protoplasm of the bacterium, and thereby the bacteria can be sterilized in a short period of time.

In addition, according to the present invention, since the sterilizing chamber, the hand piece communicating bore and the ozone decomposer are so connected by piping that after completion of a sterilizing operation among them, the ozone and oxygen gas still containing a high-concentration of residual ozone can be circulated, by repeating this circulation, each time ozone that is harmful for human bodies is decomposed into oxygen in the ozone decomposer. Therefore, even if thereafter one opens the lid of the sterilizing chamber and removes the hand piece from the chamber, there is no danger at all for human bodies and the apparatus is safe, because ozone gas would not be exhausted from the interior of the sterilizing chamber to the environmental atmosphere. Furthermore, since it is possible to open the lid and take out sterilized instruments after it has been confirmed by an ozone monitor that the ozone gas concentration has been sufficiently lowered, by coupling the ozone monitor with the ozone decomposer, there is no fear that ozone gas may flow out from the sterilizing chamber into the environmental atmosphere and hurt human bodies when the lid is opened.

What is claimed is:

1. An apparatus for sterilizing objects having a wetted surface, said apparatus comprising: a sterilizing chamber, means including an ozone generator for providing a mixture of ozone and oxygen to said sterilization chamber; a heater for heating said mixture of zone and oxygen; a first conduit means coupling said ozone generator to said heater; a second conduit means coupling said heater to one end of said sterilizing chamber; seat means in said sterilizing chamber to support a hollow piece having an opening therethrough to be internally sterilized, said seat means having a conduit element communicating through a third conduit means with an intake of the ozone generator and a recirculating pump in said third conduit means for inducing a positive flow of ozone containing gas through said seat means and any hollow piece seated thereon whereby ozone depleted gas in said third conduit is recirculated through said ozone generator and said heater, said third conduit means communicating through a first valve means with a second pump connected to a gas discharge port for withdrawing gas which has passed through said seat means, said first valve means for fluidly isolating said second pump from said seat, and a second valve means in said third conduit means for fluidly isolating said recirculating pump from said seat means when said first valve is open.

2. An apparatus for sterilizing objects having a wetted surface, said apparatus comprising: a sterilizing chamber; means including an ozone generator for providing a mixture of zone and oxygen; a heater; a first conduit coupled to said ozone generator and to said heater for heating said mixture of ozone and oxygen; a second conduit coupled to said heater and to an inlet at one end of said chamber; an outlet communicating with an end of said sterilizing chamber other than said one end; a first conduit-and-valve means communicating with said one end of said sterilizing chamber and with an inlet for said ozone generator; circulating pump means in said first conduit-and-valve means for withdrawing ozone and air from said sterilizing chamber and creating a flow of ozone and air through said sterilizing chamber and said ozone generator whereby the gaseous content of said sterilizing chamber is recycled through the ozone generator for restoring or increasing the ozone content of the gas content of said chamber and the ozone can operate as a bacterium destroying medium; and exhaust means communicating with said outlet, said exhaust means having a valve operable to release externally the gases from said chamber; seats in said sterilizing chamber to respectively support hollow pieces to be sterilized, each of said seats having a respective conduit element communicating with the interior of a respective hollow piece supported thereon, a second conduit-and-valve means for alternately directing the gas passed through said seats and pieces supported thereon to said exhaust means for exhausting ozone and air from said sterilization chamber and third valve means in said first conduit-and-valve means or for alternately recycling ozone and air from said chamber sequentially to said pump, said ozone generator, and said heater for causing the ozone and air mixture to pass through the interior of said hollow pieces for sterilizing the interior of said hollow pieces when said pieces to be sterilized are received in said seats; said exhaust means also including an exhaust port, and a second pump being provided between said seats and said exhaust port to cause the ozone and air mixture to be exhausted through said exhaust port while said third valve means is closed to fluidly isolate said circulating pump means in said first conduit-and-valve means from said seats.

3. The apparatus described in claim 2 wherein pulsing type pressure varying means is provided, said pressure varying means communicating with said sterilizing chamber for causing pulsation of the pressure of gas in said chamber.

4. The apparatus described in claim 2 wherein a pulsing means is provided in fluid communication with said sterilization chamber for repeatably changing the gas pressure in said sterilizaton chamber, providing valve means between said ozone generator and the inlet port to said sterilization chamber and additional respective valve means between said chamber and said output ports of said chamber for isolating said sterilization chamber from both the ozone generator and said exhaust means while said pulsing type pressure varying means is operative.

5. The apparatus described in claim 2 wherein said first conduit and valve means communicate with two ends of said sterilizing chamber and said valve means is arranged to selectively effect withdrawal from either one of said two ends, or both ends of said sterilizing chamber simultaneously, and to effect withdrawal of gas from said chamber through the conduit elements in said seats.

6. The apparatus as defined in claim 4, wherein said pressure varying means includes a piston and cylinder in fluid communication with said chamber for causing pulsation of the pressure in the gas chamber.

7. The apparatus as defined in claim 6, wherein said cylinder communicates with said chamber through an opening in a wall of said chamber other than those walls of the chamber having said inlet and said outlet.

* * * * *

UNITED STATES PATENT AND TRADEMARK OFFICE
CERTIFICATE OF CORRECTION

PATENT NO. : 5,120,512

DATED : June 9, 1992

INVENTOR(S) : Senichi Masuda

It is certified that error appears in the above-identified patent and that said Letters Patent is hereby corrected as shown below: Title page, item [57],
In the Abstract, line 10:
"oxygen as" should be --oxygen gas--.

Column 2, line 50:
"is mixture" should be --mixture is--.

Column 3, line 4:
Delete "are communicated" and insert therefor --communicate--.

Column 3, line 23:
After "cause" insert --it--.

Column 3, line 30:
"ozone" should be --ozonizer-- and after "ozonizer" delete --and--.

Column 3, line 31:
Delete "ozonized" and insert therefor --an ozone and--.

Column 3, line 65:
After "and" delete --, then--.

Column 4, line 48:
Delete "ozone and" and insert therefor --ozonizer--.

Column 4, line 61:
Delete "ozone and" and insert therefor --ozonizer--.

Column 4, line 64:
Delete "ozone and" and insert therefor --ozonizer--.

Column 4, line 64 and 65:
Delete "ozonized" and insert therefor --ozone and--.

Column 5, line 25:
"32)" should be --32,--.

UNITED STATES PATENT AND TRADEMARK OFFICE
CERTIFICATE OF CORRECTION

PATENT NO. : 5,120,512

DATED : June 9, 1992

INVENTOR(S) : Senichi Masuda

It is certified that error appears in the above-identified patent and that said Letters Patent is hereby corrected as shown below:

Column 5, line 37:
    Delete "ozone and" and insert therefor --ozonized--.

Column 5, line 58:
    Delete "ozone and" and insert therefor --ozonizer--.

Column 5, line 65:
    Delete "ozone and" and insert therefor --ozonizer--.

Column 6, line 4:
    Delete "ozone and" and insert therefor --ozonizer--.

Column 7, line 6:
    "the opened" should be --then opened--.

Column 7, line 8:
    Delete "ozone and" and insert therefor --ozonizer--.

Column 7, line 16:
    After "Thereby" insert --a--.

Column 7, line 21:
    Delete "ozone and" and insert therefor --ozonizer--.

Column 7, line 23:
    Delete "ozone and" and insert therefor --ozonizer--.

Column 7, line 40:
    Delete "ozone and" and insert therefor --ozonized--.

Column 7, line 47:
    Delete "ozone and" and insert therefor --ozonized--.

UNITED STATES PATENT AND TRADEMARK OFFICE
CERTIFICATE OF CORRECTION

PATENT NO. : 5,120,512

DATED : June 9, 1992

INVENTOR(S) : Senichi Masuda

It is certified that error appears in the above-identified patent and that said Letters Patent is hereby corrected as shown below:

Column 8, line 5:
    Delete "ozone and" and insert therefor --ozonizer--.

Column 8, line 21:
    Delete "ozone and" and insert therefor --ozonizer--.

Column 9, line 1, claim 1:
    "zone" should be --ozone--.

Column 9, line 9, claim 1:
    "of the" should be --of an--.

Column 9, line 26, claim 2:
    "zone" should be --ozone--.

Column 10, line 4, claim 2:
    after "means" (second occurrence) delete --or--.

Column 10, line 35, claim 5:
    "first conduit and valve" should be --conduit and first valve--.

Signed and Sealed this

Eleventh Day of January, 1994

Attest:

BRUCE LEHMAN

Attesting Officer     Commissioner of Patents and Trademarks